United States Patent
Franco, Jr. et al.

(10) Patent No.: US 7,394,385 B2
(45) Date of Patent: Jul. 1, 2008

(54) COMPREHENSIVE MONITORING SYSTEM

(75) Inventors: Thomas S. Franco, Jr., Bedford, NH (US); William G. DiMario, Clinton, MA (US)

(73) Assignee: Wellcare Systems, Inc., Bedford, NH (US)

( * ) Notice: Subject to any disclaimer, the term of this patent is extended or adjusted under 35 U.S.C. 154(b) by 111 days.

(21) Appl. No.: 10/910,263

(22) Filed: Aug. 2, 2004

(65) Prior Publication Data

US 2005/0093709 A1    May 5, 2005

Related U.S. Application Data

(60) Provisional application No. 60/491,487, filed on Jul. 31, 2003.

(51) Int. Cl.
*G08B 23/00* (2006.01)
(52) U.S. Cl. .................. 340/573.1; 340/573.7; 340/689
(58) Field of Classification Search .............. 340/573.1, 340/573.4, 573.7, 539.11, 539.12, 539.13, 340/539.16, 539.17, 539.24, 669, 689; 600/300, 600/549; 702/150, 151
See application file for complete search history.

(56) References Cited

U.S. PATENT DOCUMENTS

| | | | |
|---|---|---|---|
| 4,814,751 A | 3/1989 | Hawkins et al. | |
| 5,742,233 A | 4/1998 | Hoffman et al. | |
| 5,963,137 A | 10/1999 | Waters, Sr. | |
| 6,002,994 A | 12/1999 | Lane et al. | |
| 6,160,478 A | 12/2000 | Jacobsen et al. | |
| 6,243,039 B1 | 6/2001 | Elliot | |
| 6,307,481 B1 | 10/2001 | Lehrman et al. | |
| 6,433,690 B2 | 8/2002 | Petelenz et al. | |
| 6,501,386 B2 | 12/2002 | Lehrman et al. | |
| 6,504,503 B1 | 1/2003 | Saint-Hilaire et al. | |
| 6,595,929 B2 * | 7/2003 | Stivoric et al. | 600/549 |
| 6,605,038 B1 * | 8/2003 | Teller et al. | 600/300 |
| 6,611,783 B2 * | 8/2003 | Kelly et al. | 702/150 |
| 6,703,939 B2 * | 3/2004 | Lehrman et al. | 340/669 |
| 6,796,799 B1 * | 9/2004 | Yoshiike et al. | 434/236 |
| 6,819,247 B2 * | 11/2004 | Birnbach et al. | 340/573.1 |
| 6,873,256 B2 * | 3/2005 | Lemelson et al. | 340/539.1 |
| 6,930,608 B2 * | 8/2005 | Grajales et al. | 340/573.5 |
| 6,937,900 B1 * | 8/2005 | Pianca et al. | 607/19 |
| 6,963,301 B2 * | 11/2005 | Schantz et al. | 342/125 |
| 2003/0055606 A1 | 3/2003 | Christ et al. | |

* cited by examiner

*Primary Examiner*—Van T. Trieu
(74) *Attorney, Agent, or Firm*—Robert R Deleault, Esq.; Mesmer & Deleault, PLLC

(57) ABSTRACT

A monitoring system for physically challenged clients can have a base hub unit, one or more sensor units, one or more repeater units, and a mobile unit for a client to wear in a residential setting. In an institutional setting, a mobile repeater can be used for monitoring outside premises. A three-axis accelerometer can be used to detect falls and to monitor for other life activities, such as sleeping.

19 Claims, 10 Drawing Sheets

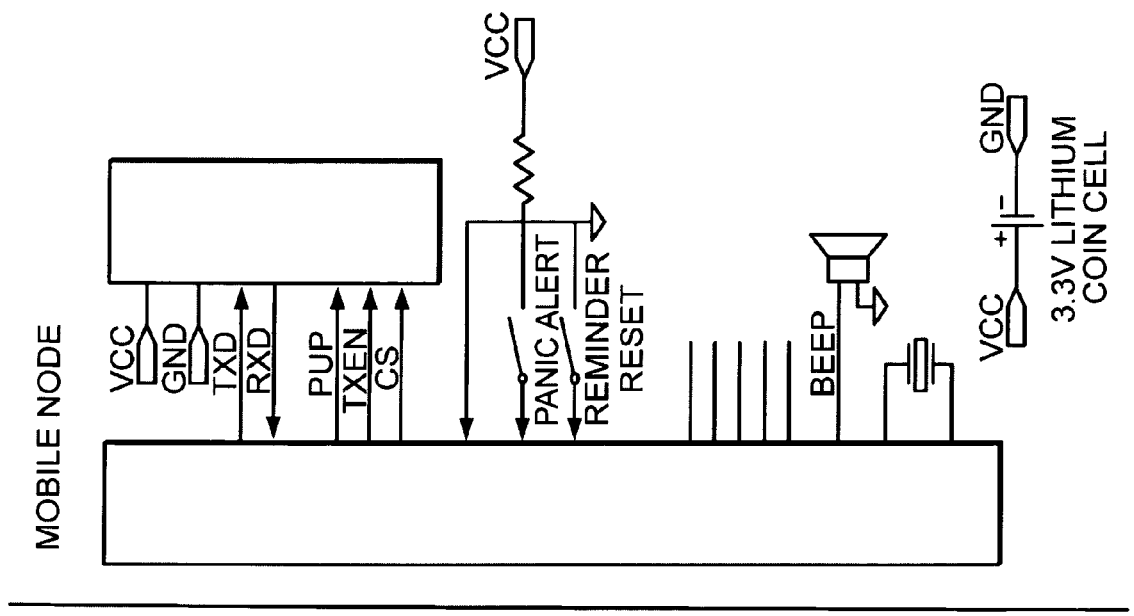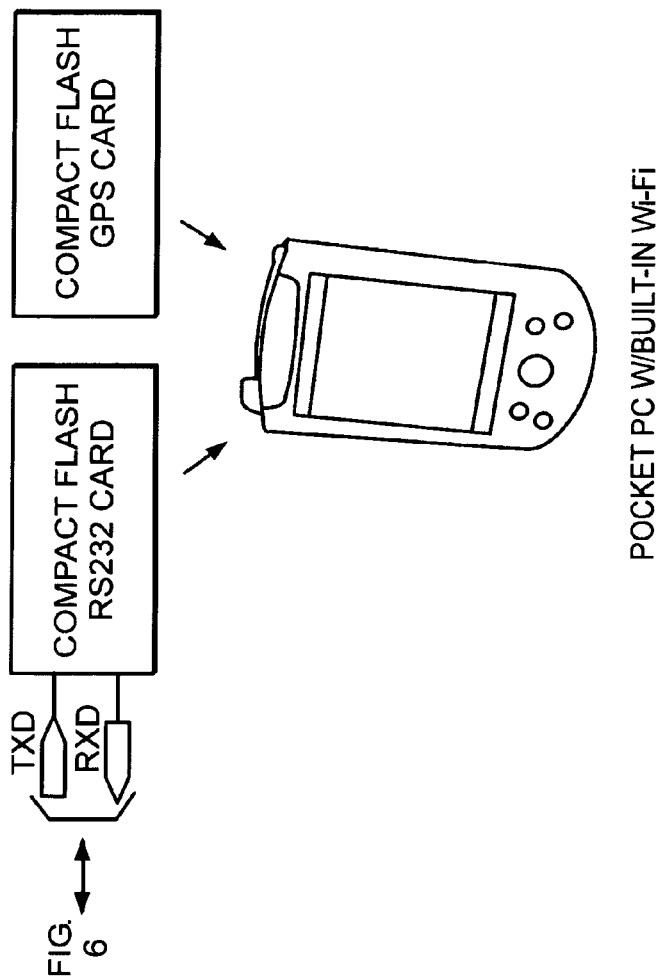
FIG. 7

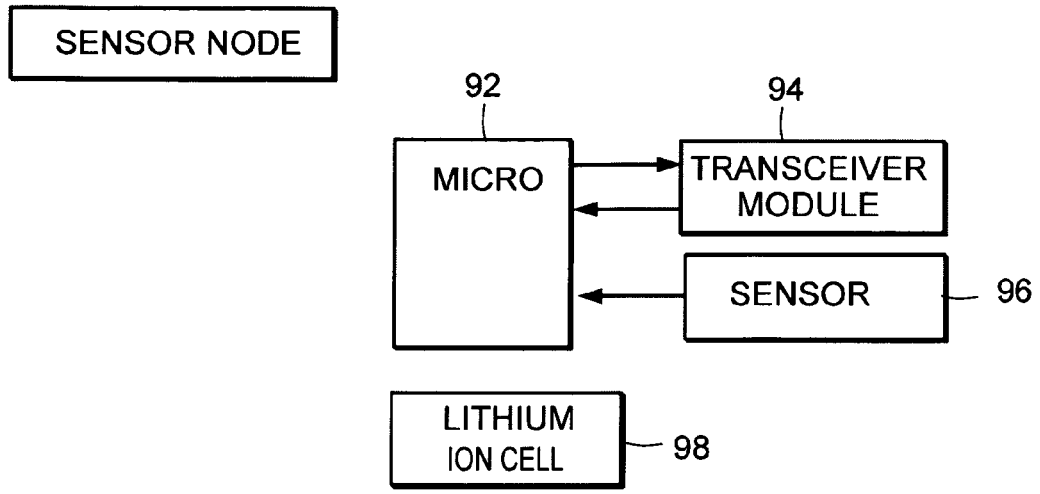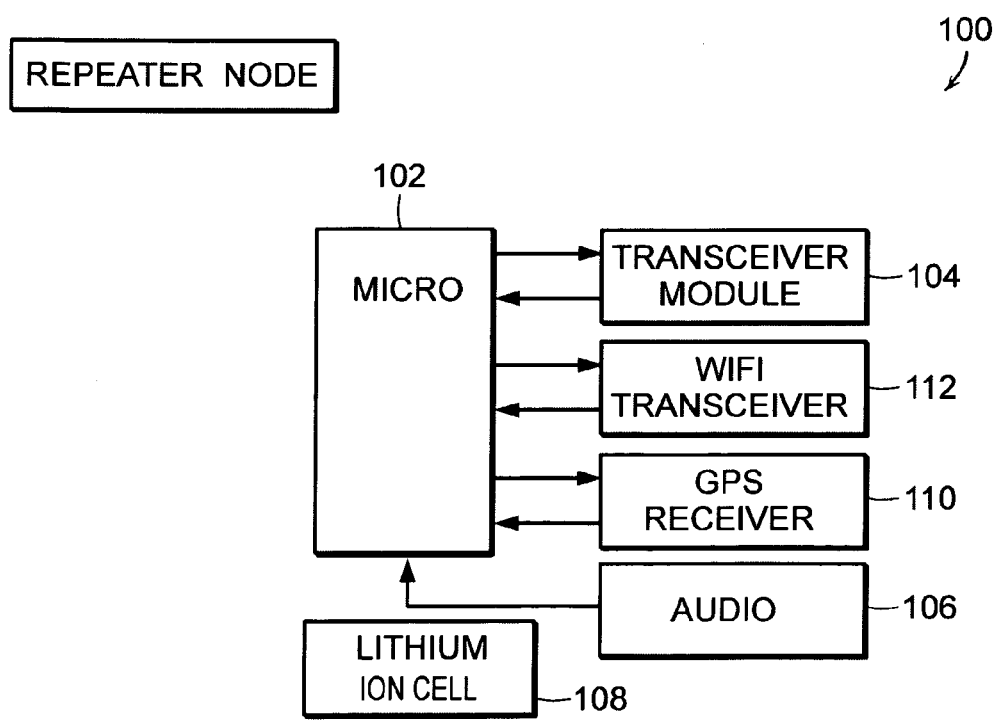
FIG. 8

COMPREHENSIVE MONITORING SYSTEM

CROSS-REFERENCE TO RELATED APPLICATION

This application claims priority to provisional application Ser. No. 60/491,487, filed Jul. 31, 2003, which is incorporated herein by reference.

BACKGROUND

Monitoring systems of the type used for elderly clients or other challenged clients should give caregivers or other family members peace of mind. Systems that rely on a wearer to push a panic button fall short of providing that comfort. A client could be unconscious or unable to press a panic button due to sudden accident or illness. An emergency situation could be overlooked, and consequently, a person's health or well-being could deteriorate more rapidly than if immediate medical attention was administered.

SUMMARY

The invention includes an alert and detection system for elderly and physically challenged clients. In disclosed embodiments, the system can have a base hub unit, one or more sensor units, one or more repeater units, and a mobile unit for a client to wear in a residential setting. In an institutional setting, a mobile repeater can be used for monitoring outside premises.

The system can integrate a number of features including a panic button, a fall detector with an accelerometer, client location monitoring with repeater nodes, client location monitoring with GPS, detection of room temperature and other ambient conditions, monitoring of appliances such as a refrigerator, toilet, or stove, and habit monitoring. When an alert is activated, a hub unit dials to a central monitoring service office or to an individual caretaker to establish a 2-way phone conversation. Multiple wireless transceivers can be provided to cover additional rooms and/or a distance from the base unit for ease of conversations.

In an embodiment generally for institutional use (such as an assisted living facility), the system can use web software, Ethernet connectivity, and global positioning. In lieu of 2-way conversations, the alerts can notify specific pagers/cell phones based on client identification and location. This feature allows for more expedient attention to alerts and eliminates the need for a central monitoring station.

Other features and advantages will become apparent from the following detailed description and drawings.

BRIEF DESCRIPTION OF THE DRAWINGS

FIGS. 3-9 are block diagrams of embodiments of nodes used in embodiments of monitoring systems.

DETAILED DESCRIPTION

Figure 1:
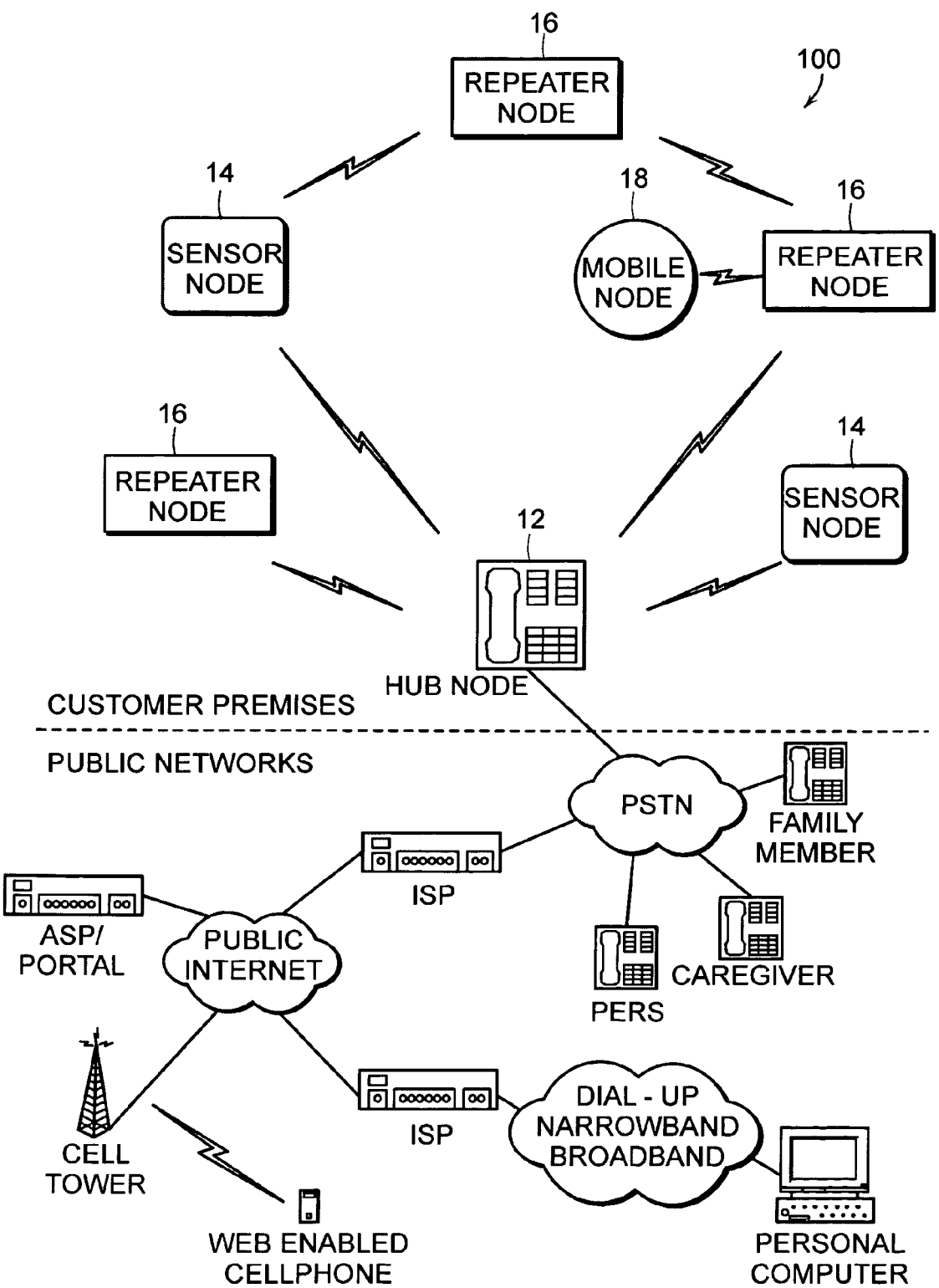
FIGS. 1, 2, and 10 are block diagrams of embodiments of monitoring systems.

Referring to FIG. 1, a monitoring system 10 has a premises side and a network side. The premises side can include hub node 12, one or more sensor nodes 14, one or more repeater nodes 16, and a mobile node 18. While explained in more detail below, generally a mobile node is worn by a client, such as in a wrist wearable device; the one or more sensor nodes are stationary and designed to sense some condition, such as the temperature in a room, or activity, such a refrigerator being opened or closed or a toilet being flushed; the repeater nodes are typically stationary in a home environment and form an ad hoc mesh network of wireless transceivers; and the hub node is primarily a communications device to communicate remotely from the care zone Multiple uniquely identified client mobile nodes can be supported in a care zone by providing each node with a unique identifier to allow collocated client mobile nodes to be monitored independently. Repeater nodes can be correlated with their physical location a priori upon installation and are distributed throughout the care zone in such a manner as to provide sufficient communication coverage. Communication with the mobile node is thus maintained through an ad hoc mesh of repeater nodes distributed throughout a care zone. Direct communication (e.g., with wired connections) to the hub node from one or more mobile nodes and one or more sensor nodes is also possible. System synchronization is maintained through beacon messages transmitted from the hub node on a regular schedule.

The hub node can communicate with the network side through the public switched telephone network (PSTN) 20 or some other remote communications method to provide a call or page directly to one or more family member, caregiver, emergency response system, and/or through an internet service provider and to the Internet. There can be a multiple party call list, e.g., to a medical practitioner and a family members, or to multiple family members.

The PSTN can also be coupled through a computer network, such as through the public Internet. A family member or caregiver can monitor the status of the client using a personal computer or a Web-enabled cellphone to access the Internet and obtain status information from a website that would preferably have appropriate security, such as passwords and encryption.

Figure 2:
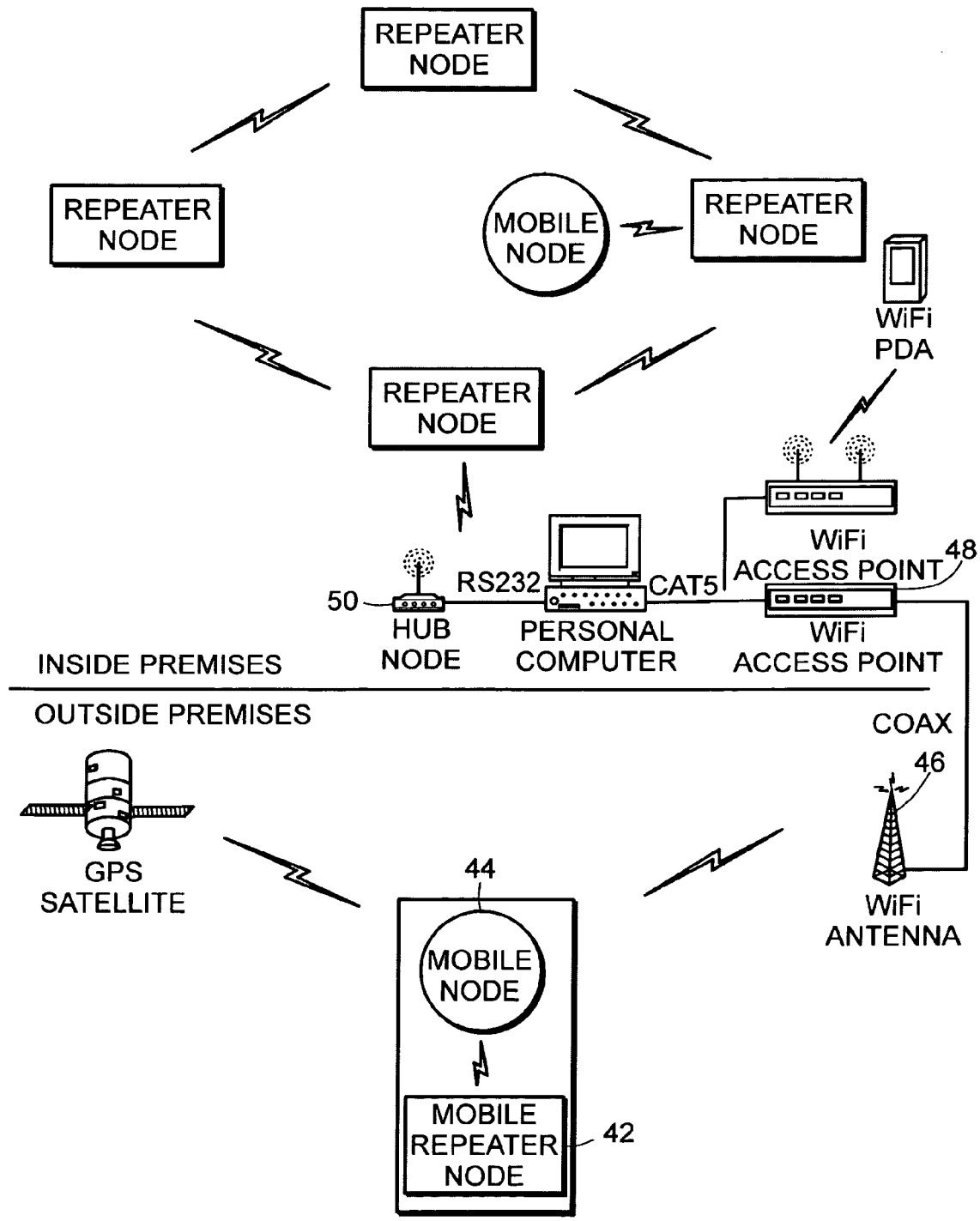

Referring to FIG. 2, in an institutional setting, referred to here as an assisted living facility (although it need not technically be one), a monitoring system 40 can include monitoring outside the premises with a mobile node 44 and mobile repeater nodes 42 to extend the system range to cover movement outside of a building. Along with fall detection and panic alert information, mobile node 44 can detect location, such as with global positioning satellite (GPS) coordinates, and transmit locational information via a WiFi back channel through a WiFi antenna 46, and to a WiFi access point 48 to a hub node 50. In a forward channel, out-of-range alerts can be sent to the mobile repeater node and mobile node. The forward channel can also convey paging and medication reminder notices.

Inside the premises, the hub node, repeater node(s), sensor node(s), and mobile node can be similar to those for the home setting, along with the network communications shown in FIG. 1. The mobile node with the mobile repeater node can also be used inside the premises to provide data through a hub.

Figure 3:
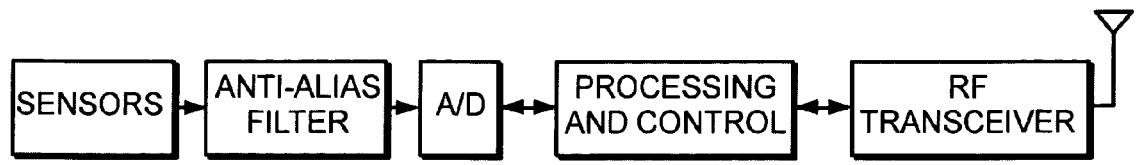
Figure 4:
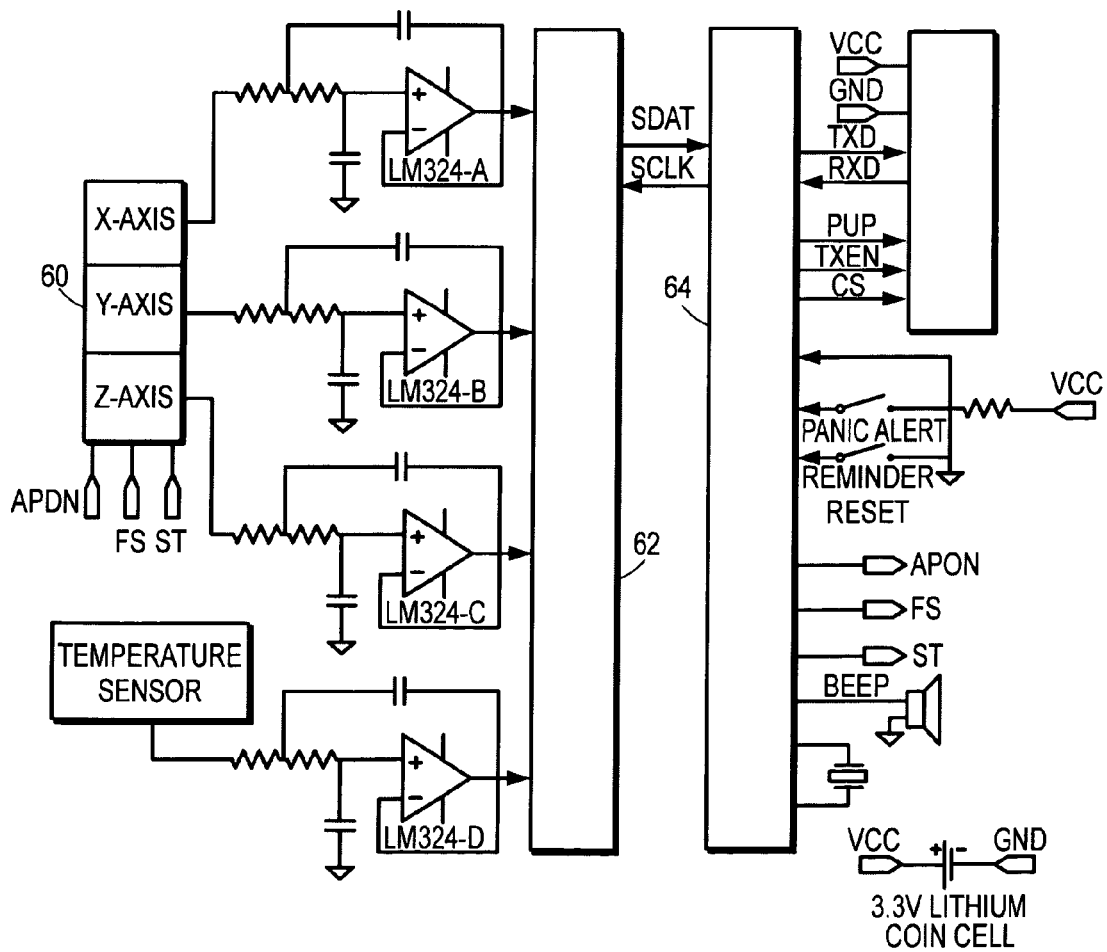

Referring to FIGS. 3 and 4, a mobile node preferably includes the following hardware and software in a portable, wearable battery powered device: a microprocessor and/or microcontroller, memory, a wireless communication port (transceiver), a user interface that can send information to and/or from a central office to the mobile node (e.g., panic button, alert indicator, beeper), sensors (e.g., multi-axis accelerometer), circuitry for sensors, and removal detection. Control software and algorithms are provided for duplex radio communication and time synchronization, battery monitoring, sensor signal conditioning and data storage, and user interface functions.

The sensor can include an accelerometer 60, such as a 3-axis model, or several accelerometers oriented to provide three-axis sensing. As shown in more detail in FIG. 4, a microprocessor continually monitors the output from the accelerometer. The data is filtered and stored until an associated repeater node polls the device. Upon polling, accelerometer data is transmitted to the hub node either directly or via the nearest repeater node. Based on the signal from the accelerometer, the system can determine whether there is a high possibility that the client fell. This determination can be made locally or remotely.

The accelerometer is designed to sense inertia in any direction. The system constructs a reference plane normal to a gravitational force vector, and normalized X-Y vectors are calculated with respect to the reference plane to allow determination of absolute and relative location when combined with the locational function of the repeater nodes (described below).

The sensor outputs are preferably filtered with a 2-pole Butterworth in a Salen-Key configuration. It may be desirable to have higher order filtering, and cascading filters can be used. A microcontroller 62 can be used as an intelligent 10 bit A/D converter with a 4-input multiplexer that allows round-robin sampling of the sensor data.

In addition to sensing a fall, accelerometer data can be used for more general monitoring purposes. For example, the accelerometer data can be used to sense minor falls that can lead to medical intervention before a client has a more serious fall. In addition, activities can be monitored in a way that would be less invasive than others (such as use of a camera). For example, accelerometer data can be used to determine if the client is sleeping well. To do this, data can be collected to determine normal patterns and deviations that can be used to create an alert. Related episodes of getting out of bed during the night, or a lack of sleep in general, or a significant change in patterns during the night, may be indication of non-restful sleep, which may be indications of other problems. For example, increased visits to a bathroom at night for a man may be an indication of a possible prostate problem.

The system thus can collect accelerometer data to establish patterns of behavior, and later pieces of accelerometer data can be compared against thresholds or against prior behavior plus thresholds to determine if there should be an alert to look further into whether there is a problem. Other habits of motion can be detected and saved as learned habits; deviations from these habits as learned through the data can be used to create an alert. In addition, trends can be observed over time as indicator that intervention may be desirable, e.g., a number of events that indicate an acceleration below the falling thresholds, but above some other threshold, or an increase in frequency in events that do not rise to the falling threshold.

In these cases and in others, an alert can cause a call to be made, a pager alert to go out, or in some cases, an alert can be more minor and can be a flag to investigate further. In addition, there can be multiple levels of alerts, e.g., immediate attention, give attention when available, or look into a situation later. If the data indicates a hard fall, immediate attention would likely be given. A questionable fall might still attract attention when available. If data appears to show a bad night's sleep without other factors, it could provide information for an aide to call the client to see how he or she is feeling.

A processor 64 is used to implement per channel FIFOs and a synchronous two-wire interface to the main control processor; this processor can be used to perform device timing, control, and radio interface through an internal USART at 19.2 Kbaud. This processor can perform low power shutdown on the radio and sensor between samples to reduce power consumption. The RF back channel is used for handshake and to send the mobile node "medication reminders" which will be annunciated to the client with a beeper. Two user switches can be used to signal "panic" and to reset a medication reminder alert.

The repeater nodes can be used to sense location of the mobile node based on the strength of signals received from the mobile node. This locational detection can be used to determine if a client is not where he/she should be, and can also be used in conjunction with the accelerometer to detect a fall. If the locational detection after a possible fall shows that the client has not moved, then an alert can be initiated. If the client does move, it is assumed the client would call for help if needed. The mobile node is preferably worn on the wrist, but it could be at the waist or at some other location.

Figure 5:
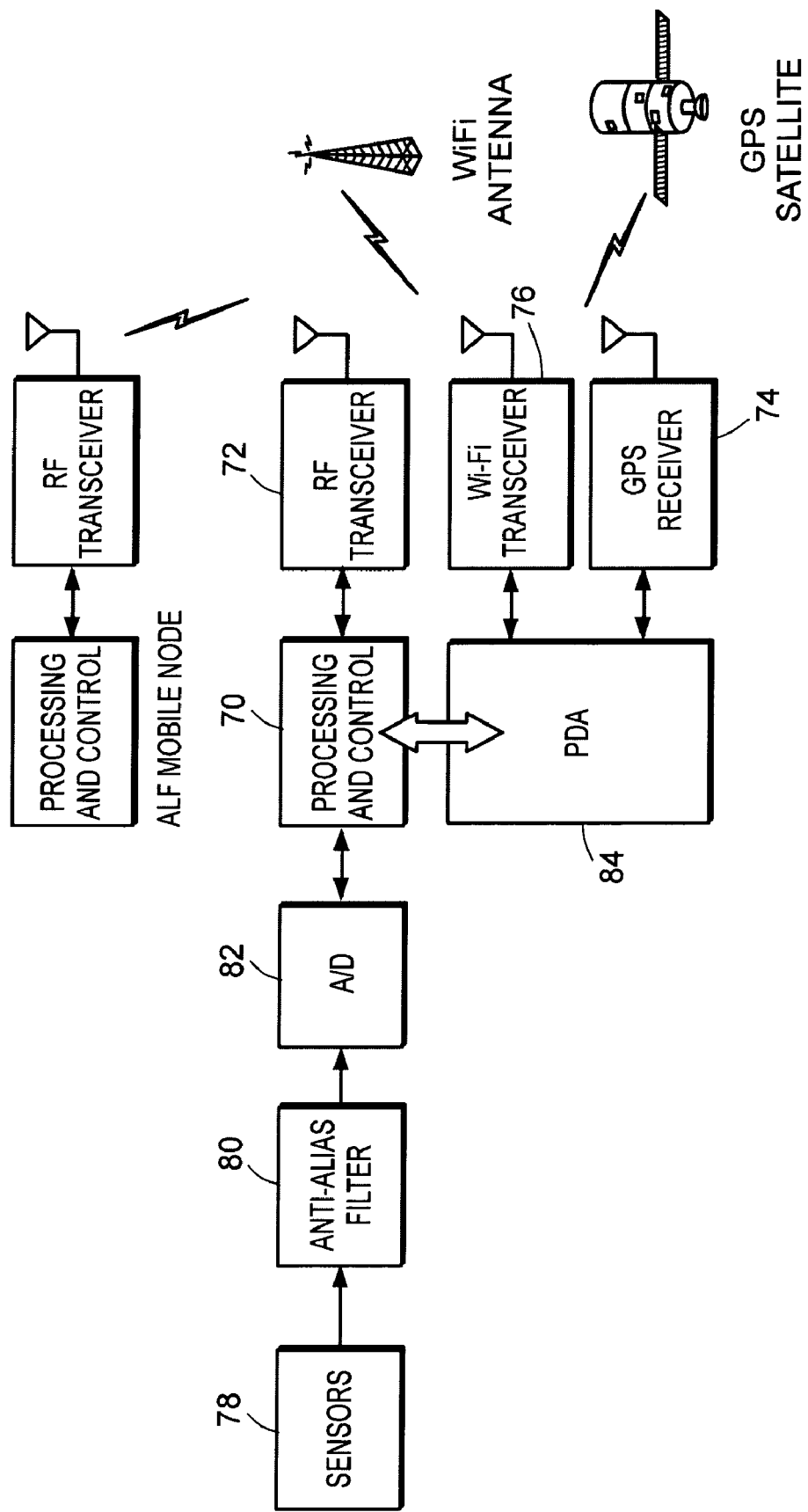
Figure 6:
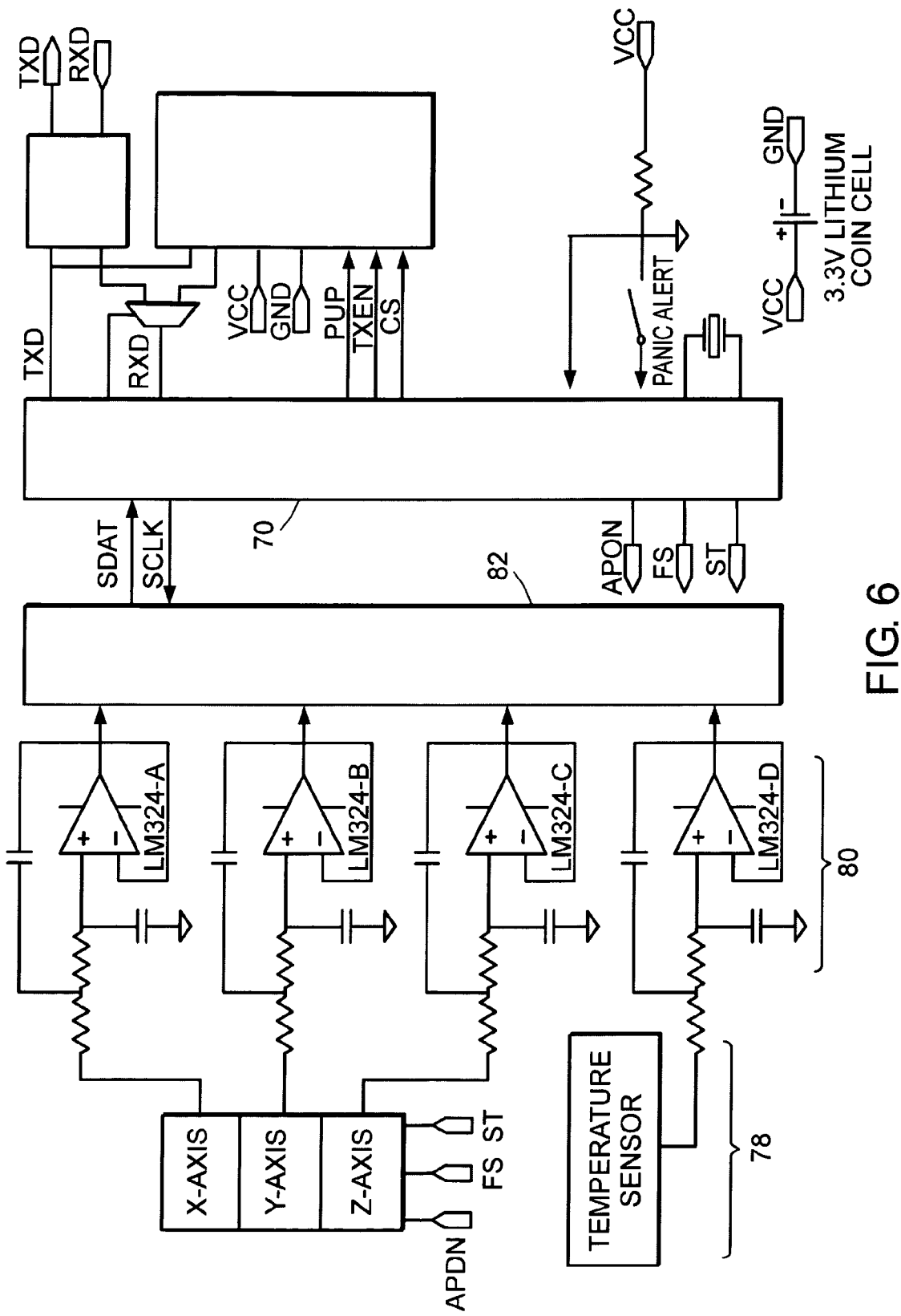

FIGS. 5-7 show a combined mobile node and mobile repeater node, such as that shown in FIG. 2. The mobile repeater is designed node for use outside premises and preferably includes the following hardware and software in a portable wearable rechargeable battery powered device: processing and control 70, memory, wireless communication port (transceiver) 72, a GPS Receiver 74, a WiFi Transceiver 76, one or more sensors 78, filtering circuits 80, an A/D converter 82, and a personal digital assistant 84.

A resident who is about to go to the outside premises of the ALF care zone uses the two nodes described here in tandem. The care zone is the coverage area of the ALF WiFi hotspot. For a client wearing a mobile node wristband or badge, the node acts as an RFID tag to uniquely identify the client to the system. A protocol can be established wherein a client validates a "sticky" association with a given mobile repeater node. This association remains for the duration of a session. When the client returns to the ALF the nodes are disassociated. This may be accomplished with simple heuristics. If the mobile node becomes "out of range" of the currently associated repeater node and the GPS location is an entry point to the building then the nodes are disassociated; otherwise an alert would be signaled.

The device may be used in conjunction with a mobile node with the components described above. The mobile node is associated with the mobile repeater node, which relays mobile node data to the hub on a regular schedule. The mobile repeater node communicates with the hub via a commercial off-the-shelf WiFi radio system, and can provide GPS information on the location of the mobile node, and hence the client.

The mobile node can freely associate the personal digital assistant (PDA) equipped with an RF transceiver. Such a PDA can be used by staff at a facility.

GPS data is one example of position data that can be used. In confined outdoor premises or in an indoor environment, other types of position data can be used, such as time of arrival systems that use triangulation to positions within a building. For example, a patient monitor may use such time of arrival data through wireless RF links to identify a patient within a building, such as a nursing home or a hospital. Such a monitor can be combined with an accelerometer to provide fall detection information in addition to determining the location of the patient.

Referring to FIG. 8, a sensor node 90 can have the following hardware and software in a stationary line powered or battery powered device: a microprocessor 92, memory, a wireless communication port (transceiver) 94, a sensor (temperature, vibration, et al.) 96, and a secondary power source 98. Control software and algorithms can perform duplex radio communication and time synchronization, battery monitoring, and sensor signal conditioning.

The microprocessor monitors the sensor output from sensor nodes, e.g., on a regular schedule. These nodes are typically stationary in the care zone. The data from the sensors is filtered and stored until an associated repeater node or hub node polls the device. Upon polling, the data is transmitted to the hub node either directly or via the nearest repeater node. The data can be processed at the hub, or transmitted to a central office for processing.

The sensor nodes can detect potentially dangerous situations, such as detecting that a stove is on for too long, temperature sensing in the room, elapsed time on/near a stove/oven. The system can also detect activity/inactivity as in indicator of wellbeing, such as by monitoring household appliances; for example, refrigerator door being opened or closed can serve as an indicator or proxy for food consumption, or toilet flushes can serve as a proxy for elimination.

Cognitive software algorithms can combine sensor data and habit/routine data to determine client wellbeing. For example, the system can use facts like refrigerator usage, stove usage, and toilet usage, or any other appliance or device in the house to determine that the client is doing well. This data can also be combined with accelerometer data to show habits and wellbeing.

Software algorithms can be used to set thresholds for alert conditions and severity based on client wellbeing and routine. The detection of appliance usage can include a learning function to determine typical use. For example, the system can look for patterns of behavior and provide a possible alert if there are deviations. If the user generally opens the refrigerator 10 times per day and the actual usage drops to once in the morning, an alert can be triggered. If the usage fluctuates widely over time, the system might look only for amounts well outside the normal usage. Sensing refrigerator usage or usage of some other accessible container can also be used to confirm that the client has likely missed taking a medication; if a medication is kept in the refrigerator and is supposed to be taken in the early evening, the system can detect that the refrigerator door was not opened in the early evening and the medication was likely not taken.

As also shown in FIG. 8, repeater node 100 preferably has the following hardware and software in a stationary device (typically line powered): microprocessor 102, memory, wireless communication port (transceiver) 104, audio communication (speaker, microphone) 106, and secondary power source 108. In a mobile repeater node, there could also be a GPS receiver 110 and WiFi transceiver 112.

Control software and algorithms can perform duplex radio communication and time synchronization.

These devices act as a relay station to provide communication coverage throughout the care zone. They also provide unique location information based on which repeater nodes receive a given signal. Because each has communications, the client can be in communication through the hub from any location, including if the client has set down the mobile node or the mobile node has become detached in an accident.

Figure 9:
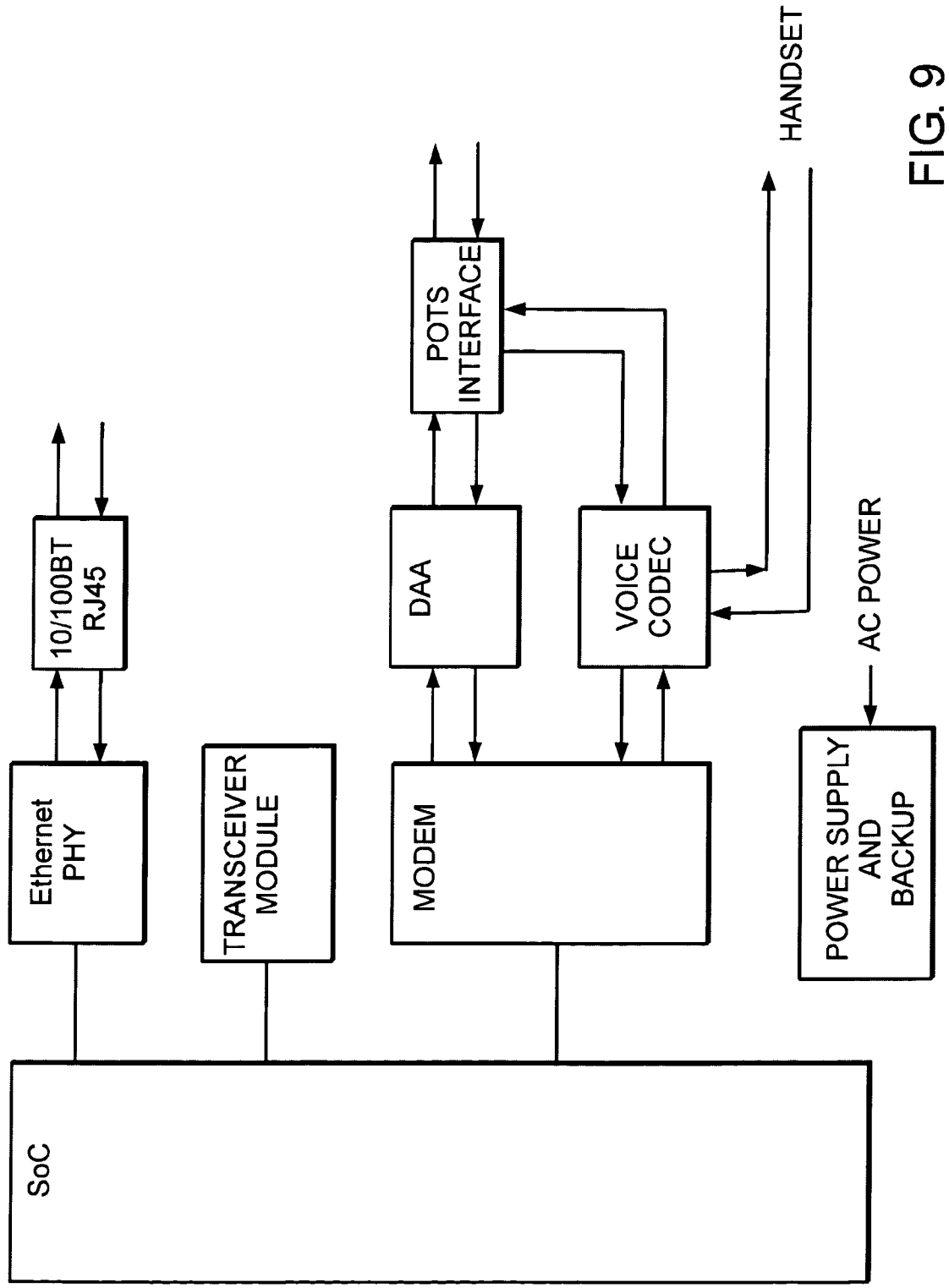

Referring to FIG. 9, a hub node can have the following in a stationary, preferably line powered, device: a microprocessor, memory, a wired communication port (POTS, Ethernet), a wireless communication port (transceiver, WiFi), audio communication (speaker, microphone), and a secondary power source.

Control software and algorithms can perform: duplex radio communication and time synchronization, maintenance of a census of mobile nodes, maintenance of a database of activity templates and thresholds, sensor data analysis to discriminate potential fall events and locomotion, emergency dialer function, and optional Ethernet communication.

In examples of nodes, a mobile node can be a wrist band, with an appearance like a watch. Repeater nodes that are located in various rooms, such as the bedroom, living room, and bathroom, can be housed in small boxes that are plugged into outlets and can be about the size of remote timers. A mobile repeater node is a small device that has about the size of a portable radio or a pager with a chip. The hub node has the appearance of a telephone and can even be integrated within a telephone.

Figure 10:
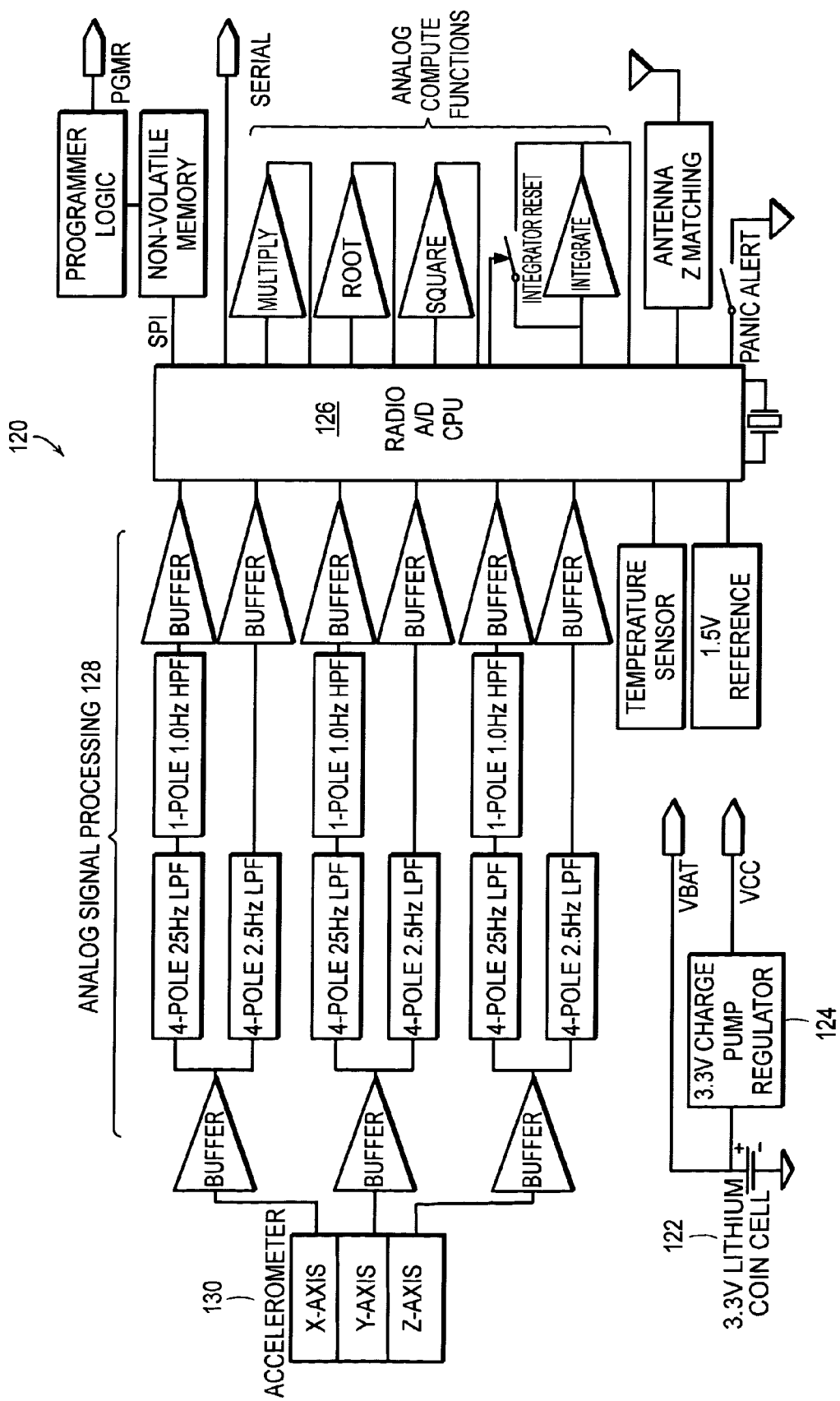

Referring to FIG. 10, another version of the device of FIG. 2 is shown. The device 120 can operate on a 3.3v lithium coin cell 122 including the sensors and filters are powered with a regulated 3.3v supply that is generated by a single switched capacitor charge pump 124. A radio chip 126 is a high integration device that includes an enhanced CPU core, an multi-channel A/D, RF transceiver and several other support peripherals. The radio chip operates from 1.9-3.6v directly from the battery. Program code for the CPU is stored in off-chip serial EEPROM and is loaded into on-chip RAM for execution at power-up. Multiple execution images may be stored in the EEPROM for upgrades and enhanced optional features.

An accelerometer 130 used to sense movement is preferably a monolithic sensor with tri-orthogonal MEMS elements. Each channel outputs a voltage that is proportional to the sensed acceleration. The analog signal processing 128 performs anti-aliasing and band limiting. There are 3 dB corners at 25 Hz, 2.5 Hz for the low pass filter and 1.0 Hz for the high pass filter. A four pole multiple feedback filter with a Butterworth response is used, although many other configurations could work, although A/D SNR and anti-aliasing requirements should be met. This filter configuration yields accurate sensing of both impact forces (dynamic acceleration) and acceleration due to gravity (static acceleration). The CPU performs additional digital signal processing on the digital data. The A/D samples the data at or above the Nyquist rate.

Figure 11:
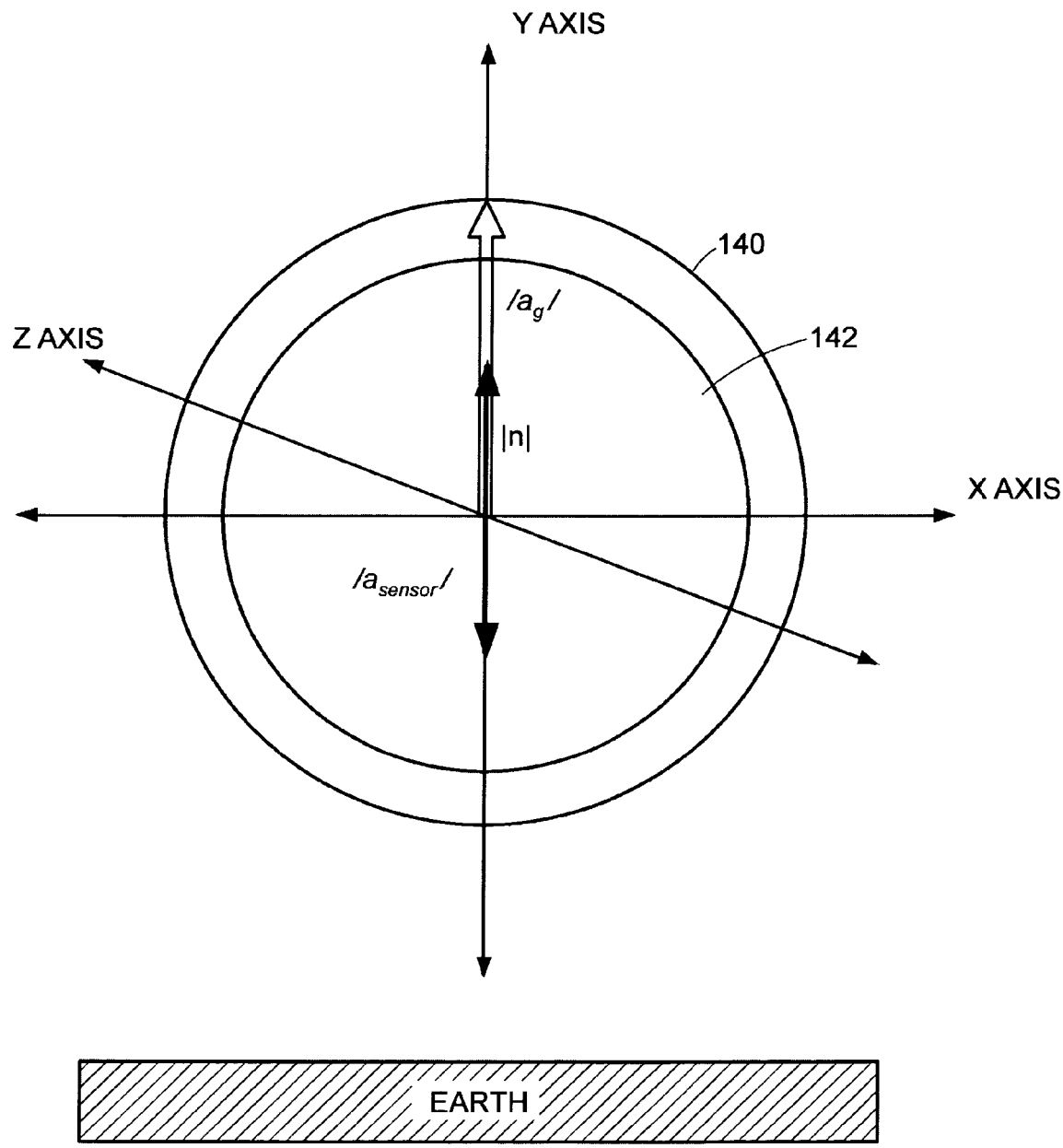
FIG. 11 shows a figure demonstrating the sensing of acceleration.

Referring to FIG. 11, the acceleration sensor outputs a voltage proportional to the sensed acceleration in each axis with some number of samples per second, e.g., 50 samples per second. Gravity acts on the accelerometer independent of its orientation, so the outer sphere 140 in FIG. 11 below represents "1G" unit sphere of |n|, normal force with no contribution of sensor acceleration.

$$|n| = \sqrt{a_{xs}^2 + a_{ys}^2 + a_{zs}^2}$$

The inner sphere 142 represents a threshold limit that the algorithm uses to determine if an accelerative event is a potential fall. If the sensor accelerates in opposition to the normal force the resulting magnitude is compared to a threshold to determine if this is a potential fall. A vertical fall is shown in FIG. 11.

Once triggered, the algorithm computes an approximate velocity of the accelerometer (approximate because acceleration components orthogonal to the normal force vector are not included).

$$v_{approximate} = \begin{cases} \int (|n| - a_g) dt & \text{if } |n| < a_{threshold} \\ v_{approximate} * k_{damping} & \text{else} \end{cases}$$

If the threshold is not exceeded then a damping factor is applied to the approximate velocity to account for system noise offsets and quantization effects in the channel.

A more accurate accelerometer velocity is computed using higher bandwidth data that has been high pass filtered to remove the static acceleration component. This velocity calculation will still be subject to quantization effects so integration is done over a finite window of time. The sample rate is adaptive depending on the filter used.

$$v_{accurate} = \sqrt{(\int a_{xd} dt)^2 + (\int a_{xd} dt)^2 + (\int a_{xd} dt)^2}$$

The "typical" fall occurs over a 500 ms-750 ms time period and is characterized by certain signature events, such as a sudden acceleration in opposition to the normal force, an accumulation of sufficient velocity which is dependent on the height of the fall, a sudden deceleration or rate of change in acceleration, and/or an impact force.

Depending on severity of the fall, movement after the fall may not occur at all or for some time. These events occur on different places in time and frequency domain. The algorithm uses a combination of band filters, sampling rates and timers to capture these events. The algorithm's thresholds and event windows are tunable parameters and can be controlled and optimized for desired sensitivity and accuracy to try to prevent false positives and false negatives.

Having described certain embodiments, it should be apparent that modifications can be made without departing from the scope of the invention as set out in the appended claims. While a number of specific microcontrollers are referred to, a processor for controlling some or all of the functions of a node can be a microprocessor, microcontroller, or any other general purpose or specific purpose programmable logic, and can be in one device or a combination of devices.

What is claimed is:

1. A client monitoring method comprising:
    using three-axis data from one or more accelerometers in a client-carried device mounted on a wrist of a client to determine if a client has fallen;
    computing an approximate velocity of the one or more accelerometers; and
    comparing the resulting approximate velocity to a threshold value wherein a damping factor is applied to the resulting approximate velocity when the resulting approximate velocity is less than the threshold value and wherein a more accurate velocity of the one or more accelerometers is calculated when the resulting approximate velocity is more than the threshold value.

2. The method of claim 1 wherein said comparing step includes applying a damping factor that has an antialiasing and median filtering applied to the resulting approximate velocity.

3. The method of claim 1 wherein said computing step includes integrating the difference between a 1 G normal force and an acceleration that opposes the normal force over a pre-determined period of time.

4. The method of claim 1 wherein said comparing step includes using higher bandwidth data that has been high-pass filtered to remove a static acceleration component when the more accurate velocity of the one or more accelerometers is calculated.

5. The method of claim 4 wherein said comparing step includes integrating the x, y and z axis acceleration of the one or more accelerometers over a pre-determined period of time when the more accurate velocity is calculated.

6. The method of claim 4 wherein the pre-determined time period is about 500 milliseconds to about 750 milliseconds.

7. The method of claim 1 further comprising providing position information to enable the determination of the location of the client.

8. The method of claim 7 wherein the providing position information step includes using a received signal strength indication that detects the signal strength to determine where the client is located and whether the client is moving.

9. The method of claim 1 further comprising using the data from the one or more accelerometers to determine information about one or more life activities other than falling.

10. The method of claim 9 further comprising comparing current accelerometer data with historic accelerometer data to determine if there is a possible wellness problem.

11. A monitoring system for monitoring a patient in a monitoring region, the system comprising:
    a mobile device with one or more accelerometers capable of providing three-axis data for detecting an acceleration by a patient when worn by a patient on the wrist wherein an algorithm uses the three-axis data to compute an approximate velocity of the one or more accelerometers and compare the approximate velocity to a threshold value wherein a damping factor is applied to the resulting approximate velocity when the resulting approximate velocity is less than the threshold value and wherein a more accurate velocity of the one or more accelerometers is calculated when the resulting approximate velocity is more than the threshold value;
    at least one sensor node disposed in a fixed geographical location within said monitoring region for detecting a physical condition in the monitoring region;
    a repeater node for transmitting signals from at least one of the mobile device and the at least one sensor node; and
    a hub node for receiving signals from the repeater node.

12. The system of claim 11 wherein the physical condition includes one of an ambient condition or a condition of a device in said monitoring region.

13. The system of claim 12 wherein the device includes one of a home appliance, a door, a toilet, a faucet, a heater, and an air conditioner and the ambient condition includes one of temperature and humidity.

14. The system of claim 11 wherein the hub node is capable of transmitting data to a location remote from the monitoring region.

15. A client monitoring method for determining a fall event, the method comprising:
    using three-axis data from one or more accelerometers contained within a client-carried device to determine if a client has fallen;
    measuring a duration of the fall event;
    measuring an impact magnitude of the fall event; and
    calculating a fall velocity of the fall event;
    computing an approximate velocity of the one or more accelerometers; and
    comparing the resulting approximate velocity to a threshold value wherein a damping factor is applied to the resulting approximate velocity when the resulting approximate velocity is less than the threshold value and wherein a more accurate velocity of the one or more accelerometers is calculated when the resulting approximate velocity is more than the threshold value.

16. The method of claim 15 further comprising measuring a recovery motion after the fall event.

17. The method of claim 15 wherein said comparing step includes applying a damping factor that has an antialiasing filtering and a median filtering applied to the resulting approximate velocity.

18. The method of claim 15 wherein said comparing step includes using higher bandwidth data that has been high-pass filtered to remove a static acceleration component when the more accurate velocity of the one or more accelerometers is calculated.

19. The method of claim 18 wherein said comparing step includes integrating the x, y and z axis acceleration of the one or more accelerometers over a pre-determined period of time when the more accurate velocity is calculated.

* * * * *